United States Patent
Tsui et al.

(10) Patent No.: US 6,344,342 B1
(45) Date of Patent: Feb. 5, 2002

(54) HUMAN G PROTEIN COUPLED LYSOPHOSPHATIDIC ACID RECEPTOR

(75) Inventors: Ping Tsui, Berwyn, PA (US); Catherine E. Ellis, Glassboro, NJ (US); Ganesh M. Sathe, King of Prussia, PA (US); Stephanie Van Horn, Pottstown, PA (US); Robert S. Ames, Havertown, PA (US); James J. Foley, Radnor, PA (US); Laura R. Fitzgerald, Kennett Square, PA (US); Henry M. Sarau, Harleyville, PA (US); Jonathan K. Chambers, Hasling Field (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/837,726

(22) Filed: Apr. 18, 2001

Related U.S. Application Data

(60) Division of application No. 09/325,897, filed on Jun. 4, 1999, now Pat. No. 6,242,572, which is a continuation-in-part of application No. 09/215,072, filed on Dec. 18, 1998, now abandoned, which is a continuation-in-part of application No. 08/992,031, filed on Dec. 17, 1997, now abandoned.
(60) Provisional application No. 60/046,366, filed on May 13, 1997.

(51) Int. Cl.[7] .............................................. C12N 15/12
(52) U.S. Cl. ................ 435/69.1; 435/252.3; 435/320.1; 536/23.5
(58) Field of Search ........................ 435/7.1, 7.2, 69.1, 435/252.3, 320.1; 536/23.5

(56) References Cited

U.S. PATENT DOCUMENTS 6,057,126 A    5/2000   Munroe et al.

FOREIGN PATENT DOCUMENTS

WO    WO 99/33972 A    7/1999

OTHER PUBLICATIONS

GenBank Accession No. U80811.
GenBank Accession No. U78192.
HGS EST: 1278414.
Bandoh et al. "Molecular cloning and Characterization of a Novel Human G–protein–coupled Receptor,EDG7, for Lysophosphatidic Acid", The Journal of Biological Chemistry, vol. 274, pp. 27776–27785 (1999).
An, et al. "Molecular Cloning of the Human Edg2 Protein and Its Identification as a Functional Cellular Receptor for Lysophosphatidic Acid", Biochemical and Biophysical Research Communications, vol. 231, pp. 619–622 (1997).
Hecht, et al., "Ventricular Zone Gene–1 (vzg–1) Encodes a Lysophosphatidic Acid Receptor Expressed in Neurogenic Regions of the Developing Cerebral Cortex", The Journal of Cell Biology, vol. 135, No. 4, pp. 1071–1083 (1996).
Oliveira, et al., "A common motif in G–protein coupled seven transmembrane helix receptors", *Journal of Computer–Aided Molecular Design*, vol. 7, pp. 649–658 (1993).
Im, et al., "Molecular Cloning and Characterization of a Lysophosphatidic Acid Receptor, Edg–7, Expressed in Prostate", Molecular Pharmacology, vol. 57, pp. 753–759 (2000).

*Primary Examiner*—John Ulm
(74) *Attorney, Agent, or Firm*—William T. Han; Ratner & Prestia; William T. King

(57) ABSTRACT

HOFNH30 polypeptides and polynucleotides and methods for producing such polypeptides by recombinant techniques are disclosed. Also disclosed are methods for utilizing HOFNH30 polypeptides and polynucleotides in terapy, and diagnostic assays for such.

13 Claims, No Drawings

US 6,344,342 B1

HUMAN G PROTEIN COUPLED LYSOPHOSPHATIDIC ACID RECEPTOR

CROSS-REFERENCE TO RELATED APPLICATIONS

This application is a division of application Ser. No. 09/325,897, filed Jun. 4, 1999, now U.S. Pat. No. 6,242,572 which is a continuation-in-part of U.S. application Ser. No. 09/215,072, filed Dec. 18, 1998, now abandoned, which is also a continuation-in-part application of U.S. Ser. No. 08/992,031, filed Dec. 17, 1997, now abandoned, which in turn claims the benefit of U.S. Provisional Application No. 60/046,366, filed May 13, 1997. All four applications are incorporated herein by reference in their entireties.

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

It is well established that many medically significant biological processes are mediated by proteins participating in signal transduction pathways that involve G-proteins and/or second messengers. e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA. 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide GPT. GPT also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane a-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the b-adrenoreceptor, phosphorylation by protein kinase A and/or specific receptor kinases mediates receptor desensitization. For some receptors, the ligand binding sites of G-protein coupled receptors are believed to comprise hydrophilic sockets formed by several G-protein coupled receptor transmembrane domains, said socket being surrounded by hydrophobic residues of the G-protein coupled receptors. The hydrophilic side of each G-protein coupled receptor transmembrane helix is postulated to face inward and form polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also inmplicated in ligand binding.

G-protein coupled receptors can be intracellulary coupled by heterotrimeric G-proteins to various intracellular enzymes, ion channels and transporters (see, Johnson et al., Endoc. Rev., 1989, 10:317–331) Different G-protein a-subunits preferentially stimulate particular effectors to modulate various biological functions in a cell. Phosphorylation of cytoplasmic residues of G-protein coupled receptors have been identified as an important mechanism for the regulation of G-protein couplings of some G-protein coupled receptors. G-protein coupled receptors are found in numerous sites within a mammalian host. Over the past 15 years, nearly 350 therapeutic agents targeting 7 transmembrane (7 TM) receptors have been successfully introduced onto the market.

SUMMARY OF THE INVENTION

The present invention relates to HOFNH30, in particular HOFNH30 polypeptides and HOFNH30 polynucleotides, recombinant materials and methods for their production. In another aspect, the invention relates to methods for using such polypeptides and polynucleotides, including the treatment of infections such as bacterial, fungal, protozoan and viral infections, particularly infections caused by HIV-1 or HIV-2; cancers; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy (benign prostatic hyperplasia); chronic renal failure; renal disease; impaired glucose tolerance; seizure disorder; depression; anxiety; obsessive compulsive disorder; affective neurosis/disorder; depressive neurosis/disorder; anxiety neurosis; dysthymic disorder; behavior disorder; mood disorder; schizophrenia; psychosexual dysfunction; sex disorder; sexual disorder; disturbed biological and circadian rhythms; feeding disorders, such as anorexia, bulimia, cachexia, and obesity; Cushing's syndrome/disease; basophil adenoma; prolactinoma; hyperprolactinemia; hypopituitarism; hypophysis tumor/adenoma; hypothalamic diseases; Froehlich's syndrome; adenohypophysis disease; hypophysis disease; hypophysis tumor/adenoma; pituitary growth hormone; adenohypophysis hypofunction; adrenohpophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, heart and lung diseases, mental illness, and addictions: migraine; hyperalgesia; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labour pain; cancer pain; post-chemotherapy pain; post-stroke pain; post-operative pain; neuralgia; and tolerance to narcotics or withdrawal from narcotics; sleep disorders; sleep apnea; narcolepsy; insomnia; parasomnia; jet-lag syndrome; and other neurodegenerative disorders, which includes nosological entities such as disinhibition-dementia-parkinsonism-amyotrophy complex; pallido-ponto-nigral degeneration; and dyskinesias, such as Huntington's disease or Gilles dela Tourett's syndrome, hereinafter referred to as "the Diseases", amongst others. In a still fturther aspect, the invention relates to diagnostic assays for detecting Diseases associated with inappropriate HOFNH30 activity or levels.

In accordance with another aspect of the present invention there are provided methods of screening for compounds which bind to and activate the HOFNH30 polypeptides (receptors) of the present invention (called agonists), or inhibit the interaction of the HOFNH30 polypeptides with receptor ligands (called antagonists). In particular, a preferred method for identifying agonist or antagonist of a receptor of the present invention comprises:
  (a) contacting a cell expressing on the surface thereof the receptor, said receptor being associated with a second component capable of providing a detectable signal in response to the binding of a compound to said receptor, with a compound to be screened under conditions to permit binding to the receptor; and
  (b) determining whether the compound binds to and activates or inhibits the receptor by measuring the level of a signal generated from the interaction of the compound with the receptor.

Further, preferred method for identifying agonist or antagonist of a receptor of the present invention comprises:
  (a) contacting a cell expressing on the surface thereof the receptor, said receptor being associated with a second component capable of providing a detectable signal in response to the binding of a compound to said receptor, with a compound to be screened under conditions to permit binding to the receptor; and
  (b) determining whether the compound binds to and activates or inhibits the receptor by comparing the level of a signal generated from the interaction of the compound with the receptor with the level of a signal without the presence of the compound.

In further preferred embodiments, the two methods described above further comprises conducting the identification of agonist or antagonist in the presence of labeled or unlabeled LPA.

In another embodiment of the method for identifying agonist or antagonist of a receptor of the present invention comprises:
  determining the inhibition of binding of a ligand to cells which have the receptor on the surface thereof, or to cell membranes containing the receptor, in the presence of a candidate compound under conditions to permit binding to the receptor, and determining the amount of ligand bound to the receptor, such that a compound capable of causing reduction of binding of a ligand is an agonist or antagonist. Preferably the ligand is LPA. Yet more preferably LPA is labeled. More particularly, a method of screening for HOFNH30 receptor antagonist or agonist comprises the steps of:
  (a) incubating a labeled LPA with a whole cell expressing HOFNH30 receptor on the cell surface, or cell membrane containing HOFNH30 receptor;
  (b) measuring the amount of labeled LPA bound to the whole cell or the cell membrane;
  (c) adding a candidate compound to a mixture of labeled LPA and the whole cell or the cell membrane of step (a) and allowing to attain equilibrium;
  (d) measuring the amount of labeled LPA bound to the whole cell or the cell membrane after step (c); and
  (e) comparing the difference in the labeled LPA bound in step (b) and (d), such that the compound which causes the reduction in binding in step (d) is an agonist or antagonist.

In still another aspect, the invention relates to agonists and antagonists discovered by the present screening methods. Yet in still another aspect, the invention relates to treating conditions associated with HOFNH30 imbalance with the identified compounds.

DESCRIPTION OF THE INVENTION

In a first aspect, the present invention relates to HOFNH30 polypeptides. Such peptides include isolated polypeptides comprising an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity. preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the EDG family of polypeptides. They are therefore of interest because this invention adds an additional member in the EDG family of genes that are involved in a number of biological and diseased manifestations. These properties are hereinafter referred to as "HOFNH30 activity" or "HOFNH30 polypeptide activity" or "biological activity of HOFNH30". Also included amongst these activities are antigenic and immunogenic activities of said HOFNH30 polypeptides, in particular the antigenic and immunogenic activities of the polypeptide of SEQ ID NO:2. Preferably, a polypeptide of the present invention exhibits at least one biological activity of HOFNH30.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to HOFNH30 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identify are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with EDG2. The nucleotide sequence of SEQ ID NO:1 is a cDNA sequence and comprises a polypeptide encoding sequence (nucleotide1 to 1065) encoding a polypeptide of 354 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the EDG family, having homology and/or structural similarity with EDG2. Preferred polypeptides and polynucleotides of the present invention are expected to have, inter alia, similar biological functions/properties to their homologous polypeptides and polynucleotides. Furthermore, preferred polypeptides and polynucleotides of the present invention have at least one HOFNH30 activity.

Polynucleotides of the present invention may be obtained, using standard cloning and screening techniques, from a cDNA library derived from mRNA in cells of human Placenta, using the expressed sequence tag (EST) analysis (Adams, M. D., et al. *Science* (1991) 252:1651–1656; Adams, M. D. et al., *Nature,* (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of SEQ ID NO: 1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10 % dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the potypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characterized by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HOFNH30 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., *Science* (1985) 230:1242). Sequence changes at specific locations may also be revealed by nuclease protection assays, such as RNase and S1 protection or the chemical cleavage method (see Cotton et al., *Proc Natl Acad Sci USA* (1985) 85: 4397–4401). In another embodiment, an array of oligonucleotides probes comprising HOFNH30 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the HOFNH30 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:
(a) a polynucleotide of the present invention, preferably the nucleotide sequence of SEQ ID NO: 1, or a fragment thereof;
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly infections such as bacterial, fungal, protozoan and viral infections, particularly infections caused by HIV-1 or HIV-2; cancers; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy (benign prostatic hyperplasia); chronic renal failure; renal disease; impaired glucose tolerance; seizure disorder; depression; anxiety; obsessive compulsive disorder; affective neurosis/disorder; depressive neurosis/disorder; anxiety neurosis; dysthymic disorder; behavior disorder; mood disorder; shizophrenia; psychosexual dysfunction; sex disorder; sexual disorder; disturbed biological and circadian rhythms; feeding disorders, such as anorexia,. bulimia, cachexia, and obesity; Cushing's syndrome/disease; basophil adenoma; prolactinoma; hyperprolactinemia; hypopituitarism; hypophysis tumor/adenoma; hypothalamic diseases; Froehlich's syndrome; adenohypophysis disease; hypophysis disease; hypophysis tumor/adenoma; pituitary growth hormone; adenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, heart and lung diseases, mental illness, and addictions; migraine; hyperalgesia; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labour pain; cancer pain; post-chemotherapy pain; post-stroke pain; post-operative pain; neuralgia; and tolerance to narcotics or withdrawal from narcotics; sleep disorders; sleep apnea; narcolepsy; insomnia; parasomrnia; jet-lag syndrome; and other neurodegenerative disorders, which includes nosological entities such as disinhibition-dementia-parkinsonism-amyotrophy complex; pallido-ponto-nigral degeneration; and dyskinesias, such as Huntington's disease or Gilles dela Tourett's syndrome, amongst others.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

We have now discovered that LPA is a ligand for HOFNH30 polypeptide. The HOFNH30 polypeptide of the present invention may be employed in a process for screening for compounds which bind to and activate the HOFNH30 polypeptides of the present invention (called agonists), or inhibit the interaction of the HOFNH30 polypeptides with receptor ligands (called antagonists).

Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., Current Protocols in Immunology 1(2):Chapter 5 (1991).

HOFNH30 proteins are responsible for many biological functions, including many pathologies. Accordingly, it is desirous to find compounds and drugs which stimulate HOFNH30 on the one hand and which can inhibit the function of HOFNH30 on the other hand. In general, agonists or antagoinsts, as the case may be, are employed for therapeutic and prophylactic purposes for such conditions as infections such as bacterial, fungal, protozoan and viral infections, particularly infections caused by HIV-1 or HIV-2; cancers; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy (benign prostatic hyperplasia); chronic renal failure;

renal disease; impaired glucose tolerance; seizure disorder; depression; anxiety; obsessive compulsive disorder; affective neurosis/disorder; depressive neurosis/disorder; anxiety neurosis; dysthymic disorder; behavior disorder; mood disorder; shizophrenia; psychosexual dysfunction; sex disorder; sexual disorder; disturbed biological and circadian rhythms; feeding disorders; such as anorexia, bulimia, cachexia, and obesity; Cushing's syndrome/disease; basophil adenoma; prolactinoma; hyperprolactinemia; hypopituitarism; hypophysis tumor/adenoma; hypothalamic diseases; Froehlich's syndrome; adenohypophysis disease; hypophysis disease; hypophysis tumor/adenoma; pituitary growth hormone; adenohypophysis hypofunction; adrenohpophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism, gigantism; acromegaly; disturbed biological and circadian rhythms; and sleep disturbances associated with such diseases as neurological disorders, heart and lung diseases, mental illness, and addictions, migraine: hyperalgesia; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labour pain; cancer pain; post-chemotherapy pain; post-stroke pain; post-operative pain; neuralgia; and tolerance to narcotics or withdrawal from narcotics; sleep disorders; sleep apnea; narcolepsy; insomnia; parasomnia; jet-lag syndrome; and other neurodegenerative disorders, which includes nosological entities such as disinhibition-dementia-parkinsonism-amyotrophy complex; pallido-ponto-nigral degeneration; and dyskinesias, such as Huntington's disease or Gilles dela Tourett's syndrome.

In general, such screening procedures involve providing appropriate cells which express the receptor polypeptide of the present invention on the surface thereof. Such cells include cells from mammals, yeast, Drosophila or *E. coli*. In particular, a polynucleotide encoding the receptor of the present invention is employed to transfect cells to thereby express the HOFNH30 polypeptide. The expressed receptor is then contacted with a test compound to observe binding, stimulation or inhibition of a functional response.

One such screening procedure involves the use of melanophores which are transfected to express the HOFNH30 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor. Other screening techniques include the use of cells which express the HOFNH30 polypeptide (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the HOFNH30 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the HOFNH30 polypeptide such that the cell expresses the receptor on its surface. The cell is then contacted with a potential antagonist or agonist in the presence of a labeled form of a ligand, such as LPA. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, Xenopus Oocytes, RBL-2H3, etc) which are tnansfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, Xenopus Oocytes, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as LPA, and the signal produced by the reporter gene is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonits involves introducing RNA encoding the HOFNH30 polypeptide into Xenopus oocytes (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for HOFNH30 polypeptide inhibitors by determining inhibition or stimulation of HOFNH30 polypeptide-mediated cAMP and/or adenylate cyclase accumulation or dimunition. Such a method involves transiently or stably transfecting a eukaryotic cell with HOFNH30 polypeptide receptor to express the receptor on the cell surface. The cell is then exposed to potential antagonists or agonists in the presence of HOFNH30 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits HOFNH30 polypeptide-ligand binding, the levels of HOFNH30 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as HOFNH30, along with a mixture comprised of mammalian expression plasmids cDNAs encoding G$\alpha$15 (Wilkie T. M. et al Proc Natl Acad Sci USA 1991 88:10049–10053), G$\alpha$16 (Amatruda T. T. et al Proc Natl Acad Sci USA 1991 8:5587–5591, and three chimeric G-proteins refered to as Gqi5, Gqs5, and Gqo5 (Conklin B R et al Nature 1993 363:274–276, Conklin B. R. et al Mol Pharmacol 1996 50:885–890). Following a 24 h incubation the transfected HEK-293 cells are plated into poly-D-lysine coated 96 well black/clear plates (Becton Dickinson, Bedford, Mass.). The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G$\alpha$15, G$\alpha$16, Gqi5, Gqs5, or Gqo5. If the GPCR requires the presence of one of the G-proteins for functional expression in HEK-293 cells, all subsequent experiments are performed with HEK-293 cell co-transfected with the GPCR and the G-protein which gives the best response. Alternatively, the receptor can be expressed in a different cell line, for example RBL-2H3, without additional G-proteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATa. Each cell type secretes a small peptide hormone that binds to a G-protein coupled receptor on opposite mating-type cells which triggers a MAP kinase cascade leading to GI arrest as a prelude to cell fusion. Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclin-dependent kinases leading to cell cycle arrest; and (iii) construction of reporter genes fused to the FUS1 gene promoter (where FUS1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometnc readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J. Nature 384: 14–16, 1996; Manfredi et al., Mol. Cell. Biol. 16: 4700–4709, 1996). This provides a rapid direct growth selection (e.g, using the FUS1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands. Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUS1-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

The present invention also provides a method for identifying new ligands not known to be capable of binding to an HOFNH30 polypeptides. The screening assays described above for identifying agonists may be used to identify new ligands.

The present invention also contemplates agonists and antagonists obtainable from the above described screening methods.

Examples of potential HOFNH30 polypeptide receptor antagonists include peptidomimetics, synthetic organic molecules, natural products, antibodies, etc. which bind to the receptor but do not elicit a second messenger response such that the activity of the receptor is prevented.

Potential antagonists also include proteins which are closely related to the ligand of the HOFNH30 polypeptide receptor, i.e. a fragment of the ligand, which have lost biological function, and when they bind to the HOFNH30 polypeptide receptor, elicit no response.

Potential antagonists also includes a small molecule which binds to the HOFNH30 polypeptide receptor, making it inaccessible to ligands such that normal biological activity is prevented. Examples of small molecules include, but are not limited to, small peptides or peptide-like molecules.

Potential antagonists also include soluble forms of HOFNH30 polypeptide receptor, e.g., fragments of the receptor, which bind to the ligand and prevent the ligand from interacting with membrane bound HOFNH30 polypeptide receptors.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix-see Lee, et al., Nucl. Acids Res., 6: 3073 (1979); Cooney, et al, Science, 241: 456 (1988); and Dervan, et al., Science, 251: 1360 (1991)), thereby preventing transcription and production of a HOFNH30 polypeptide. The antisense RNA oligonucleotide hybridizes to the MRNA in vivo and blocks translation of the mRNA molecule to a HOFNH30 polypeptide (antisense-Okano, J., Neurochem., 56: 560 (1991); OLIGODEOXYNUCLEOTIDES AS ANTISENSE INHIBITORS OF GENE EXPRESSION, CRC Press, Boca Raton, Fla. (1988)). The oligonucleotides described above can also be delivered to cells such that the antisense RNA or DNA may be expressed in vivo to inhibit production of a HOFNH30 polypeptide.

Thus in another aspect, the present invention relates to a screening kit for identifying agonists, antagonists, and ligands for HOFNH30 polypeptides, which comprises:
(a) a HOFNH30 polypeptide, preferably that of SEQ ID NO:2; and further preferably comprises labeled or unlabeled LPA;
(b) a recombinant cell expressing a HOFNH30 polypeptide, preferably that of SEQ ID NO:2; and further preferably comprises labeled or unlabeled LPA; or
(c) a cell membrane expressing HOFNH30 polypeptide; preferably that of SEQ ID NO:2; and further preferably comprises labeled or unlabeled LPA.

It will be appreciated that in any such kit, (a), (b), or (c) may comprise a substantial component.

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}I$), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:
(a) a polypeptide of the present invention;
(b) a recombinant cell expressing a polypeptide of the present invention;
(c) a cell membrane expressing a polypeptide of the present invention; or
(d) antibody to a polypeptide of the present invention; which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesizing candidate compounds that are predicted to bind to or react with the deduced binding or reactive site; and
(d) testing whether the candidate compounds are indeed agonists, antagonists or inhibitors.

It will be further appreciated that this will normally be an interactive process.

In a further aspect, the present invention provides methods of treating abnormal conditions such as, for instance, infections such as bacterial, fungal, protozoan and viral infections, particularly infections caused by HIV-1 or HIV-2; cancers; diabetes; asthma; Parkinson's disease; both acute and congestive heart failure; hypotension; hypertension; urinary retention; osteoporosis; angina pectoris; myocardial infarction; ulcers; asthma; allergies; benign prostatic hypertrophy (benign prostatic hyperplasia); chronic renal failure; renal disease; impaired glucose tolerance; seizure disorder; depression; anxiety; obsessive compulsive disorder; affective neurosis/disorder; depressive neurosis/disorder; anxiety neurosis; dysthymic disorder; behavior disorder; mood disorder; shizophrenia; psychosexual dysfunction; sex disorder; sexual disorder; disturbed biological and circadian rhythms; feeding disorders, such as anorexia, bulimia, cachexia, and obesity; Cushing's syndrome/disease; basophil adenoma; prolactinoma; hyperprolactinemia; hypopituitarism; hypophysis tumor/adenoma; hypothalamic diseases; Froehlich's syndrome; adenohypophysis disease; hypophysis disease; hypophysis tumor/adenoma; pituitary growth hormone; adenohypophysis hypofunction; adrenohpophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, heart and lung diseases, mental illness, and addictions; migraine; hyperalgesia; enhanced or exaggerated sensitivity to pain, such as hyperalgesia, causalgia and allodynia; acute pain; burn pain;

atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labour pain; cancer pain; post-chemotherapy pain; post-stroke pain; post-operative pain; neuralgia; and tolerance to narcotics or withdrawal from narcotics; sleep disorders; sleep apnea; narcolepsy; insomnia; parasomnia; jet-lag syndrome; and other neurodegenerative disorders, which includes nosological entities such as disinhibition-dementia-parkinsonism-amyotrophy complex; pallido-ponto-nigral degeneration; and dyskinesias, such as Huntington's disease or Gilles dela Tourett's syndrome, related to either an excess of, or an under-expression of, HOFNH30 polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the HOFNH30 polypeptide.

In still another approach, expression of the gene encoding endogenous HOFNH30 polypeptide can be inhibited using expression blocking techniques. Known such techniques involve the use of antisense sequences, either internally generated or separately administered (see, for example, O'Connor, *J Neurochem* (1991) 56:560 in Oligodeoxynucleotides as Antisense Inhibitors of Gene Expression. CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

For treating abnormal conditions related to an under-expression of HOFNH30 and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of HOFNH30 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fasidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS-STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual,* Altschul, S., et al., NCBI NLM NIH Bethesda, Md.

20894; Altschul, S., et al., *J Mol. Biol.* 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

As used herein LPA refers to 1-Oleoyl-sn-glycero-3-phosphate or L-alpha-Lysophosphatidic acid, oleoyl with the chemical structure

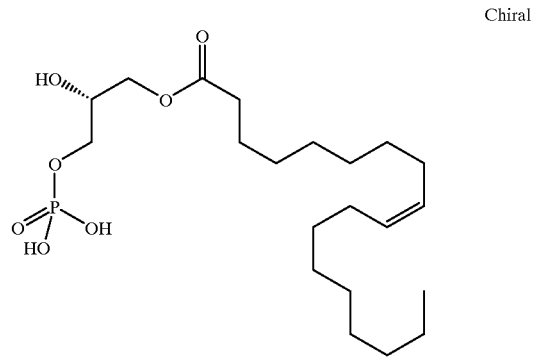

All publications, including but not limited to patents and patent applications, cited in this specification are herein incorporated by reference as if each individual publication were specifically and individually indicated to be incorporated by reference herein as though fully set forth.

EXAMPLES

Example 1
Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Example 2

Ligand Bank for Binding and Functional Assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 3

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards its receptor. Assay conditions for buffers, ions, pH and other modulators such as nucliotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 4

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml. Ovarian lobes are removed from adult female toads. Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 6

Extract/Cell Supernatant Screening

A large number of mammalian receptors exist for which there remains, as yet, no cognate activating liganid (agonist). Thus, active ligands for these receptors may not be included within the liauids banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified.

Example 8

Calcium and cAMP Functional Assays

7TM, receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue cell extracts are evaluated for agonist induced calcium mobilization. Similarly, HEK 293 cells expressing recombinant receptors are evaluated for the stimulation or inhibition of cAMP production using standard cAMP qualititation assays. Agonists presenting a calcium transient or cAMP flucuation are tested in vector control cells to determine if the response is unique to the taansfected cells expressing receptor.

Example 9

Description of FLIPR Assay in which HNFH30 was Paired with LPA

A microtitre plate based $Ca_2^+$-miobilization FLIPR assay (Fluorescent Imaging Plate Reader, Molecular Devices, Sunnyvale, Calif.) was used for the functional identification of the ligand activating RBL-2H3 cells stably expressing HOFNH30. Cells were plated in a poly-D-lysine coated 96 well black/clear plates (Becton Dickinson, Bedford, Mass.). After 18–24 h the media was aspirated and Fluo 3AM-loaded cells (Molecular Probes, Eugene, Oreg.) were exposed to several bioactive lipids, including LPA. After initiation of the assay, fluorescence was read every 1s for 1 min and then every 3 s for the following 1 min. Several clones of RBL-2H3 cells stably expressing HOFNH30 exhibited a dose dependent calcium mobilization response to LPA.

What is claimed is:

1. An isolated polynucleotide comprising a nucleotide sequence encoding a polypeptide that comprises the amino acid sequence set forth in SEQ ID NO:2.

2. The isolated polynucleotide of claim 1 wherein the polynucleotide encodes a polypeptide consisting of the amino acid sequence set forth in SEQ ID NO:2.

3. An expression vector comprising a polynucleotide encoding a polypeptide comprising the amino acid sequence set forth in SEQ ID NO:2 when said expression vector is present in a compatible host cell.

4. A process for producing a recombinant host cell comprising transforming or transfecting a cell with the expression vector of claim 3 such that the recombinant host cell, under appropriate culture conditions, produces a polypeptide comprising the amino acid sequence set forth in SEQ ID NO:2.

5. A recombinant host cell produced by the process of claim 4.

6. A membrane of a recombinant host cell of claim 5 expressing a polypeptide comprising the amino acid sequence set forth in SEQ ID NO:2.

7. A process for producing a polypeptide comprising culturing a host cell of claim 5 under conditions sufficient for the production of said polypeptide and recovering the polypeptide from the culture.

8. An isolated polynucleotide comprising a nucleotide sequence encoding at least 50 contiguous amino acids from the amino acid sequence set forth in SEQ ID NO:2.

9. The isolated polynucleotide of claim 8 comprising a nucleotide sequence encoding at least 100 contiguous amino acids from the amino acid sequence set forth in SEQ ID NO:2.

10. The isolated polynucleotide of claim 9 comprising a nucleotide sequence encoding at least 200 contiguous amino acids from the amino acid sequence set forth in SEQ ID NO:2.

11. The isolated polynucleotide of claim 10 comprising a nucleotide sequence encoding at least 300 contiguous amino acids from the amino acid sequence set forth in SEQ ID NO:2.

12. An isolated polynucleotide comprising the polynucleotide sequence set forth in SEQ ID NO:1.

13. The isolated polynucleotide of claim 12 wherein the polynucleotide consists of the polynucleotide sequence set forth in SEQ ID NO:1.

* * * * *

SEQUENCE LISTING

<160> NUMBER OF SEQ ID NOS: 2

<210> SEQ ID NO 1
<211> LENGTH: 1065
<212> TYPE: DNA
<213> ORGANISM: HOMO SAPIEN

<400> SEQUENCE: 1

| | | | | | |
|---|---|---|---|---|---|
| atgaatgagt | gtcactatga | caagcacatg | gactttttt | ataataggag | caacactgat | 60 |
| actgtcgatg | actggacagg | aacaaagctt | gtgattgttt | tgtgtgttgg | gacgttttc | 120 |
| tgcctgttta | ttttttttc | taattctctg | gtcatcgcgg | cagtgatcaa | aaacagaaaa | 180 |
| tttcatttcc | ccttctacta | cctgttggct | aatttagctg | ctgccgattt | cttcgctgga | 240 |
| attgcctatg | tattcctgat | gtttaacaca | ggcccagttt | caaaaacttt | gactgtcaac | 300 |
| cgctggtttc | tccgtcaggg | gcttctggac | agtagcttga | ctgcttccct | caccaacttg | 360 |
| ctggttatcg | ccgtggagag | gcacatgtca | atcatgagga | tgcgggtcca | tagcaacctg | 420 |
| accaaaaaga | gggtgacact | gctcattttg | cttgtctggg | ccatcgccat | ttttatgggg | 480 |
| gcggtcccca | cactgggctg | gaattgcctc | tgcaacatct | ctgcctgctc | ttccctggcc | 540 |
| cccatttaca | gcaggagtta | ccttgttttc | tggacagtgt | ccaacctcat | ggccttcctc | 600 |
| atcatggttg | tggtgtacct | gcggatctac | gtgtacgtca | agaggaaaac | caacgtcttg | 660 |
| tctccgcata | caagtgggtc | catcagccgc | cggaggacac | ccatgaagct | aatgaagacg | 720 |
| gtgatgactg | tcttagggc | gtttgtggta | tgctggaccc | caggcctggt | ggttctgctg | 780 |
| cttgatggcc | tgaactgtac | gcagtgtggc | gtgcagcatg | tcaaaaggtg | gttcctgctg | 840 |
| ctggcgctgc | tgaactctgt | catgaacccc | atcatctact | cctacaagga | cgaggacatg | 900 |
| tacagcacca | tgaagaagat | gatctgctgc | ttctctcagg | agaggaacct | ggacagacgt | 960 |
| ccctcccgcc | tcccctccac | catcctcagc | aggagcgaca | cgggcagcca | gtataaggaa | 1020 |
| gacagtagca | gccaaggcac | ggtttgcaac | aagaacagtt | cctaa | | 1065 |

<210> SEQ ID NO 2
<211> LENGTH: 354
<212> TYPE: PRT
<213> ORGANISM: HOMO SAPIENS

<400> SEQUENCE: 2

Met Asn Glu Cys His Tyr Asp Lys His Met Asp Phe Phe Tyr Asn Arg
1               5                   10                  15

Ser Asn Thr Asp Thr Val Asp Asp Trp Thr Gly Thr Lys Leu Val Ile
            20                  25                  30

Val Leu Cys Val Gly Thr Phe Phe Cys Leu Phe Ile Phe Phe Ser Asn
        35                  40                  45

Ser Leu Val Ile Ala Ala Val Ile Lys Asn Arg Lys Phe His Phe Pro
    50                  55                  60

Phe Tyr Tyr Leu Leu Ala Asn Leu Ala Ala Ala Asp Phe Phe Ala Gly
65                  70                  75                  80

Ile Ala Tyr Val Phe Leu Met Phe Asn Thr Gly Pro Val Ser Lys Thr
                85                  90                  95

Leu Thr Val Asn Arg Trp Phe Leu Arg Gln Gly Leu Leu Asp Ser Ser
            100                 105                 110

Leu Thr Ala Ser Leu Thr Asn Leu Leu Val Ile Ala Val Glu Arg His
        115                 120                 125

-continued

```
Met Ser Ile Met Arg Met Arg Val His Ser Asn Leu Thr Lys Lys Arg
    130                 135                 140
Val Thr Leu Leu Ile Leu Leu Val Trp Ala Ile Ala Ile Phe Met Gly
145                 150                 155                 160
Ala Val Pro Thr Leu Gly Trp Asn Cys Leu Cys Asn Ile Ser Ala Cys
                165                 170                 175
Ser Ser Leu Ala Pro Ile Tyr Ser Arg Ser Tyr Leu Val Phe Trp Thr
            180                 185                 190
Val Ser Asn Leu Met Ala Phe Leu Ile Met Val Val Tyr Leu Arg
        195                 200                 205
Ile Tyr Val Tyr Val Lys Arg Lys Thr Asn Val Leu Ser Pro His Thr
        210                 215                 220
Ser Gly Ser Ile Ser Arg Arg Thr Pro Met Lys Leu Met Lys Thr
225                 230                 235                 240
Val Met Thr Val Leu Gly Ala Phe Val Val Cys Trp Thr Pro Gly Leu
                245                 250                 255
Val Val Leu Leu Leu Asp Gly Leu Asn Cys Thr Gln Cys Gly Val Gln
            260                 265                 270
His Val Lys Arg Trp Phe Leu Leu Leu Ala Leu Leu Asn Ser Val Met
        275                 280                 285
Asn Pro Ile Ile Tyr Ser Tyr Lys Asp Glu Asp Met Tyr Ser Thr Met
    290                 295                 300
Lys Lys Met Ile Cys Cys Phe Ser Gln Glu Arg Asn Leu Asp Arg Arg
305                 310                 315                 320
Pro Ser Arg Leu Pro Ser Thr Ile Leu Ser Arg Ser Asp Thr Gly Ser
                325                 330                 335
Gln Tyr Lys Glu Asp Ser Ser Ser Gln Gly Thr Val Cys Asn Lys Asn
                340                 345                 350
Ser Ser
```